United States Patent [19]
Rosow et al.

[11] Patent Number: 5,966,210
[45] Date of Patent: Oct. 12, 1999

[54] APPARATUS FOR EVALUATING THE PERFORMANCE CHARACTERISTICS OF ENDOSCOPES

[75] Inventors: Eric Rosow, Avon; Curtis Youndahl; Finton Beatrice, both of Vernon, all of Conn.

[73] Assignee: Hartford Hospital, Hartford, Conn.

[21] Appl. No.: 08/821,601

[22] Filed: Mar. 20, 1997

[51] Int. Cl.$^6$ .............................. G01J 1/00; A61B 1/00
[52] U.S. Cl. ........................................... 356/213; 600/102
[58] Field of Search ..................................... 356/213, 221; 385/137, 58; 382/141; 312/209; 248/121, 122.1, 125.3, 125.7, 112; 600/102; 604/163, 171, 192

[56] References Cited

U.S. PATENT DOCUMENTS

| | | | |
|---|---|---|---|
| 4,349,014 | 9/1982 | Takamatsu | 128/6 |
| 4,375,818 | 3/1983 | Suwaki et al. | 128/660 |
| 4,402,311 | 9/1983 | Hattori | 128/4 |
| 4,562,344 | 12/1985 | Mihara et al. | 250/201 |
| 4,579,230 | 4/1986 | Reid, Jr. | 211/13 |
| 4,590,924 | 5/1986 | Tanikawa et al. | 128/6 |
| 4,621,618 | 11/1986 | Omagari | 128/6 |
| 4,686,964 | 8/1987 | Yunoki et al. | 128/4 |
| 4,742,815 | 5/1988 | Ninan et al. | 128/6 |
| 4,930,861 | 6/1990 | Okabe et al. | 350/96.25 |
| 4,996,975 | 3/1991 | Nakamura | 128/6 |
| 5,045,934 | 9/1991 | Kikuchi | 358/98 |
| 5,270,825 | 12/1993 | Takasugi et al. | 358/209 |
| 5,337,731 | 8/1994 | Takahashi et al. | 128/4 |
| 5,444,574 | 8/1995 | Ono et al. | 359/708 |
| 5,469,840 | 11/1995 | Tanii et al. | 600/117 |
| 5,503,320 | 4/1996 | Webster et al. | 227/176.1 |
| 5,539,971 | 7/1996 | Kelly | 29/418 |
| 5,545,120 | 8/1996 | Chen et al. | 600/117 |
| 5,679,110 | 10/1997 | Hamazaki | 600/124 |

*Primary Examiner*—Frank G. Font
*Assistant Examiner*—Michael P. Stafira
*Attorney, Agent, or Firm*—McCormick, Paulding & Huber

[57] ABSTRACT

In an apparatus for evaluating the performance characteristics of fiber optic endoscopes, a frame defines a carrier support, and an upstanding arm support mounted rearwardly of and adjacent to the carrier support. A plurality of targets are supported on a carrier movable along the carrier support, and an angularly adjustable mounting arm for supporting an endoscope is pivotally coupled to the arm support for movement relative to the plurality of targets supported on the carrier. A bracket is supported on the mounting arm and is adjustable in an axial direction of the mounting arm to accommodate endoscopes of different lengths. A plurality of endoscope holders are each receivable within the bracket on the mounting arm and each holder defines a different diameter corresponding to a respective endoscope for holding endoscopes of different configurations. Each of the targets supported on the carrier is configured to perform a different test for evaluating the performance characteristics of both the lens and fiber optic wires of the endoscope. The tests include a reflective loss in fibers test; a reflective symmetry test; a lighted optic fibers test; a geometric distortion test; and a modulation transfer function test.

16 Claims, 6 Drawing Sheets

APPARATUS FOR EVALUATING THE PERFORMANCE CHARACTERISTICS OF ENDOSCOPES

FIELD OF THE INVENTION

The present invention relates generally to apparatus for testing optical equipment, and deals more particularly with an apparatus for testing and evaluating the performance characteristics of fiber optic endoscopes.

CROSS REFERENCE TO RELATED APPLICATIONS

Some of the matter contained herein is disclosed in U.S. patent application Ser. No. 08/821,112, entitled "METHOD AND APPARATUS FOR EVALUATING THE PERFORMANCE CHARACTERISTICS OF ENDOSCOPES" (Attorney Docket No. 5509-01); U.S. patent application Ser. No. 08/821,601, entitled "METHOD AND APPARATUS FOR PERFORMING MODULATION TRANSFER FUNCTION TESTS ON ENDOSCOPES" (Attorney Docket No. 5509-02); and U.S. patent application Ser. No. 08/822,283, entitled "AUTOMATED METHOD AND APPARATUS FOR EVALUATING THE PERFORMANCE CHARACTERISTICS OF ENDOSCOPES" (Attorney Docket No. 5509-04), each of which is being filed on even date herewith, is assigned to the Assignee of the present invention, and is hereby expressly incorporated by reference as part of the present disclosure.

BACKGROUND OF THE INVENTION

A typical endoscope comprises a cylindrical stainless steel case enclosing a bundle of fiber optic wires which transmit light from a distal end (tip end) to a proximal end of the endoscope. A fiber optic cable delivers light from a light source into the case through an aperture situated near the proximal end of the endoscope. The fiber optic wires transmit the light through to the distal end, where the light exits the endoscope and illuminates the area near the distal end. The endoscope in turn transmits an image of that area through the fiber optic wires to an eyepiece lens at the proximal end. A video camera coupled to the eyepiece converts the image into electronic signals and transmits the signals to a video monitor, where the image is displayed.

Endoscopes are used most often in "minimally invasive surgery", in which an endoscope is inserted into a patient, allowing a surgeon to illuminate and view the interior of the patient with minimal penetration. The use of endoscopic surgery is growing, in large part because it is generally safer and less expensive than conventional surgery, and patients tend to require less time in a hospital after endoscopic surgery. As endoscopic surgery becomes more common, there is an increasing need to accurately evaluate the performance characteristics of endoscopes.

To accurately test the optical performance of an endoscope, both the lens and the fiber optic wires should be evaluated. For example, some fiber optic wires may be damaged and only partially transmit light. In addition, the lens may distort images or blur the sharpness of image colors. These and other shortcomings in the optical performance of endoscopes may be the result of imperfections in the manufacturing process and/or may develop as the endoscope is used over time.

A further complication is that endoscopes vary in length, diameter and tip angle, which is the angle between the direction of view of the longitudinal axis of the endoscope. A system for evaluating endoscope performance ideally would be able to test and evaluate the performance characteristics of both the lens and fiber optic wires of an endoscope, and have the further capability of accommodating endoscopes having varying physical characteristics.

SUMMARY OF THE INVENTION

The present invention is directed to an apparatus for evaluating the performance characteristics of fiber optic endoscopes. The apparatus comprises a frame including a carrier support. A mounting arm for supporting an endoscope is coupled to the frame and movable relative to the carrier support to adjust the position of an endoscope supported on the mounting arm. A carrier is mounted on the carrier support adjacent to the mounting arm for movement relative to the arm. The carrier preferably includes a plurality of targets for performing optical tests for evaluating the performance characteristics of both the lens and fiber optic wires of an endoscope. In the preferred embodiment of the invention, a first support bracket is coupled to the mounting arm, and a plurality of endoscope holders are provided, each for receiving and retaining a differently sized endoscope.

The first support bracket is preferably selectively positioned along an elongated or axial direction of the mounting arm to accommodate endoscopes of different lengths. To accomplish this, the mounting arm may define an elongated slot in the axial direction for slidably receiving the first support bracket. Alternatively, the mounting arm may define a plurality of apertures spaced apart at predetermined intervals relative to each other for adjustably securing the first support bracket to the mounting arm at each interval.

The present invention also includes means for guiding the carrier along the carrier support adjacent to the mounting arm. In the preferred embodiment, the means includes a guide formed by either the carrier or carrier support, and a corresponding groove defined by the other for slidably receiving the guide.

Also in the preferred embodiment of the invention, each of the targets mounted on the carrier is adapted to perform at least one of the following tests: a reflective loss in fibers test; a reflective symmetry test; a lighted optic fibers test; a geometric distortion test; and a modulation transfer function test. Accordingly, one such target is a reflector that defines a mirror-like surface for reflecting light back into the distal end of an endoscope for performing the lighted optic fibers test. The carrier preferably includes an adjustment mechanism for varying the position of the reflector's mirror-like surface relative to the distal end of the endoscope. The other targets include a photometer for performing the relative light loss in fibers test, a reflectance card for performing the reflective symmetry and geometric distortion tests, and a semi-transparent medium for performing the modulation transfer function test.

One advantage of the present invention is that a plurality of differently sized endoscopes can be accommodated and tested using a single apparatus.

Another advantage of the present invention is that the angular position of the mounting arm is adjustable relative to the carrier and the targets mounted on the carrier so that endoscopes having different tip angles can be accommodated.

Still a further advantage of the present invention is that the carrier can accommodate a plurality of different targets allowing for several different tests to be performed using a single set-up.

BRIEF DESCRIPTION OF THE DRAWINGS

These and other features, aspects, and advantages of the present invention will become better understood with regard to the following description, appended claims, and accompanying drawings where:

DETAILED DESCRIPTION OF THE PREFERRED EMBODIMENT

Figure 1:
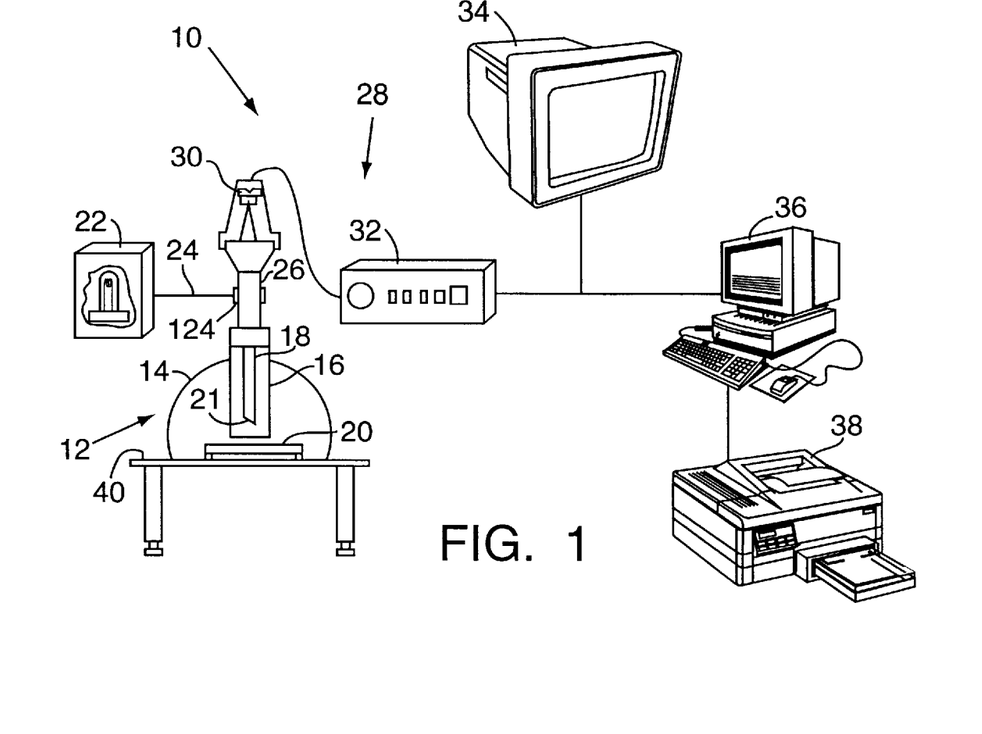
FIG. 1 is a simplified schematic of a system for evaluating the performance characteristics of fiber optic endoscopes including an apparatus embodying the present invention for testing endoscopes of different physical and optical configurations.

As shown in FIG. 1, a system for evaluating the performance characteristics of fiber optic endoscopes is indicated generally by the reference numeral 10. The system 10 includes an apparatus 12 embodying the present invention for testing any of a plurality of different endoscopes, preferably for evaluating the performance characteristics of the lens and fiber optic wires of each endoscope. The apparatus 12 is also configured to accept a plurality of different endoscopes having different physical and optical characteristics, such as different diameters, lengths and tip angles. The apparatus 12 includes a frame 14, a mounting arm 16 coupled to the frame for supporting an endoscope 18 to be tested, and a carrier 20, preferably having four quadrants, each receiving a target for performing a respective optical test. The term "target" is used herein to broadly describe any of the various devices used for receiving and/or reflecting a transmitted beam as part of each of the tests for evaluating the performance characteristics of the endoscopes. As is described further below, the carrier 20 is selectively positionable along the frame 14 adjacent to a distal end 21 of the endoscope 18, for aligning the targets used in performing the respective tests relative to each endoscope.

A high-intensity, variable light source 22, such as a xenon arc, or a halogen lamp delivers light along a fiber optic cable 24 which is detachably connected to the endoscope at its proximal end 26 in order to generate and transmit a beam of light defining a predetermined intensity pattern through the endoscope. As explained in greater detail below, the fiber optic cable 24 can also be detached from the endoscope and positioned to illuminate a selected target mounted on the carrier 20.

A video system 28 generates signals indicative of the image which is projected through an eyepiece of the endoscope in order to evaluate the performance characteristics of the endoscope based on the image data. In the preferred embodiment, the video system 28 comprises a charge-coupled device (CCD) video camera 30 and a video signal processor 32. As is well known in the art, the CCD video camera records an image by storing charges in a plurality of semiconductor potential wells. Each charge in a well corresponds to a point in the image, also known as a pixel. The video signal processor 32 transfers the charges out of the wells and thereby generates time-varying signals indicative of the recorded image. The CCD video camera 30 is coupled to the endoscope eyepiece with an adjustable vice having a lens system with both zoom and focus control rings. Thus, the projected image may be properly zoomed and focused through the vice lens system before it is recorded by the camera.

The video system 28 transmits the signals indicative of the image projected by the tested endoscope through to a video monitor 34 which displays the image, and also to a computer 36 which processes the received signals. The computer system 36 is connected to a printer 38 for printing images processed by the computer.

Figure 2:
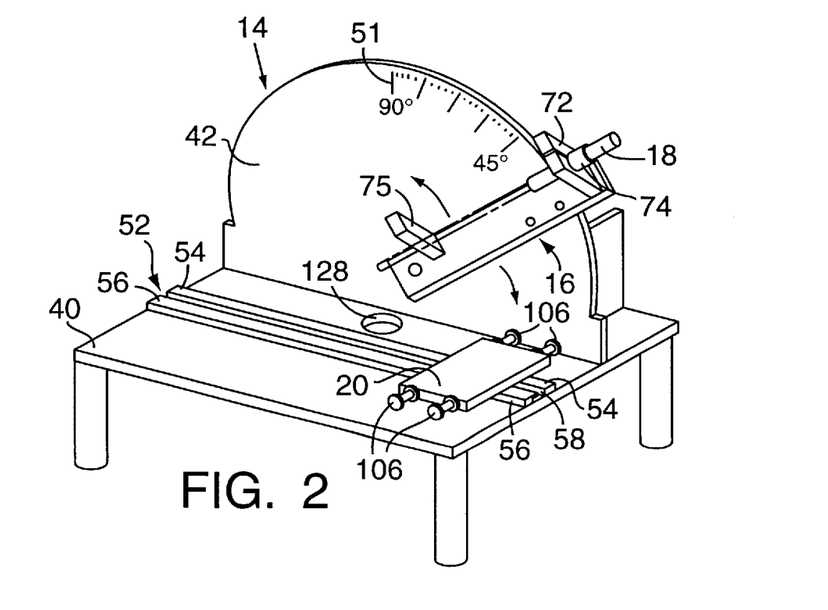
FIG. 2 is a perspective view of the apparatus embodying the present invention of FIG. 1, with parts removed for clarity.

Referring to FIG. 2, in order to use the apparatus 12 to test endoscopes having different tip angles, the distal end of each endoscope being tested must be properly aligned relative to a respective target on the carrier 20. To facilitate this alignment, the frame 14 includes a carrier support 40 and an upstanding arm support 42 mounted rearwardly of and adjacent to the carrier support.

Figure 4A:
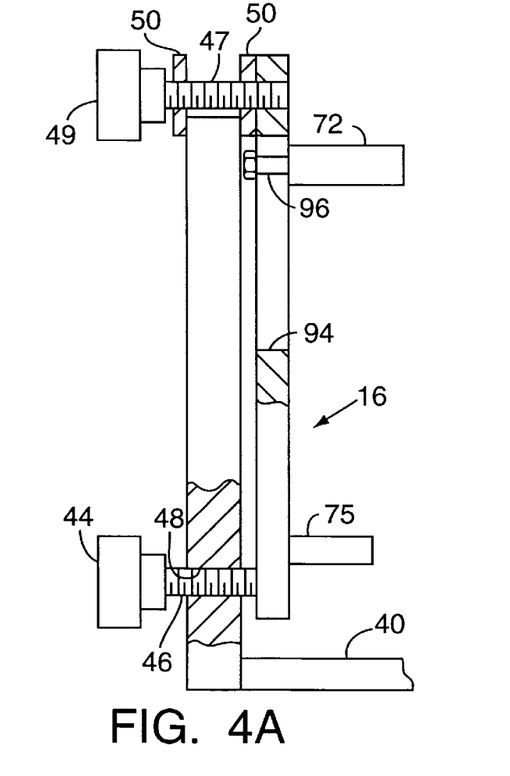
FIG. 4A is a partly in section side elevational view of the mounting arm coupled to the arm support of the apparatus of FIG. 2, taken from the left side.

As best seen in FIG. 4A, the mounting arm 16 is pivotally coupled to the arm support 42 by an adjustable first hand-knob 44 for adjusting the angular position of the mounting arm relative to the carrier support 40. A first threaded shaft 46 is connected at one end to the first hand-knob 44, extends through an aperture 48 defined by the arm support 42, and is in turn threadedly received at its other end by the mounting arm 16. A second threaded shaft 47 is threadedly received at one end by the upper end of the mounting arm 16, and at its other end by a second hand-knob 49. The second threaded shaft 47 extends from the mounting arm 16 above an upper edge of the arm support 42. A pair of washers 50 are mounted on the second threaded shaft 47, one being interposed between the arm support 42 and the mounting arm 16, and the other between the second hand-knob 49 and a rear surface of the arm support. Once the mounting arm 16 is angularly adjusted to a selected position corresponding to the tip angle of the endoscope being tested, rotation of the first hand-knob 44 causes the knob to engage the arm support 42, and rotation of the second hand-knob 49 causes the pair of washers 50 to engage the arm support at its upper edge, thereby locking the mounting arm 16 in place. The mounting arm 16 is unlocked by rotating the first and second hand-knobs 44 and 49, respectively, in a direction opposite to that required to lock the arm in place.

As shown in FIG. 2, to further aid in the proper positioning of the mounting arm 16, and of the endoscope being tested relative to the targets on the carrier 20, the arm support 42 preferably defines angular indicia 51 incrementally spaced in an arcuate pattern adjacent to its upper edge. When an endoscope is tested, the mounting arm 16 is aligned with the angular indicia 51 corresponding to the endoscope's tip angle, thereby properly positioning the endoscope relative to the targets mounted on the carrier 20. While the mounting arm 16 of the present invention has been shown and described as being pivotally coupled to the arm support 42, the invention is not limited in this regard and other methods of coupling the mounting arm to the frame for movement relative to the carrier and its associated targets may be substituted for the one illustrated. For example, the mounting arm 16 could be coupled directly to the carrier support 40.

Figure 3:
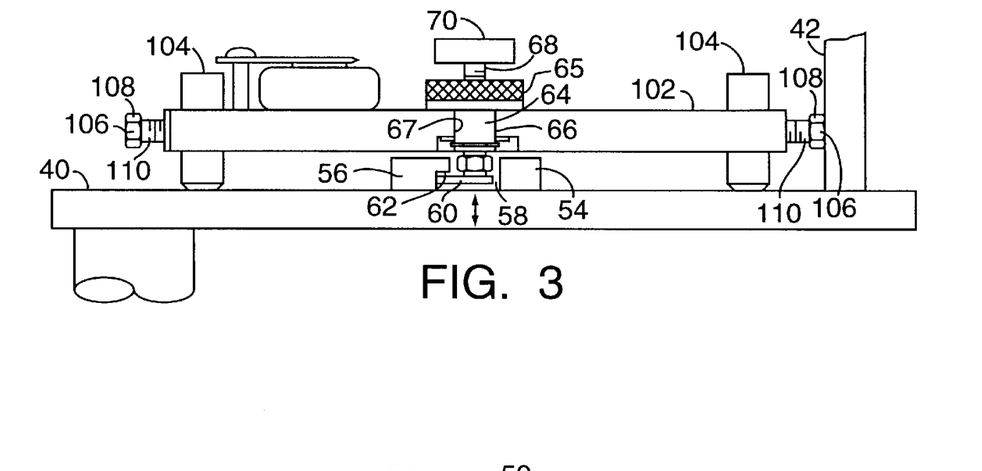
FIG. 3 is a side elevational view of the carrier of the apparatus of FIG. 2, taken from the right side.

As best seen in FIG. 2, the frame 14 also includes means 52 for guiding the carrier 20 along the carrier support 40 relative to the mounting arm 16. Preferably, means 52 includes a groove defined by one of the carrier 20 and carrier support 40, and the other defines a guide received within the groove. In the preferred embodiment, a first rail 54 is mounted on the carrier support 40 and is spaced in front of and extends approximately parallel to the arm support 42. A second rail 56 is also mounted on the carrier support 40 and is approximately parallel to, and spaced apart from the first rail 54, such that the first and second rails, 54 and 56 respectively, define a groove 58. As shown in FIG. 3, the carrier 20 includes a guide, preferably in the form of a depending foot 60 receivable within the groove 58, and as indicated by the arrows in FIG. 3, movable between an unlocked position where the foot 60 is spaced below a lip 62 of the second rail 56 for sliding the carrier along the groove, and a locked position with the foot 60 moved into engagement with the lip 62 for fixing the position of the carrier 20 along the groove. The mechanism by which the foot 60 is moved between the locked and unlocked positions includes a bushing 64 having a first cylindrical section 65 defining a knurled surface, and a second cylindrical section 66 having a reduced outer diameter in comparison to the first cylindrical section, the second cylindrical section being rotatably received within an aperture 67 extending through the carrier 20. A shaft 68 is connected on one end to the foot 60, is threaddedly received through the bushing 64, and is connected on its other end to a knob 70. By rotating the knob 70 one quarter turn, the foot 60 is rotated until it abuts the rail 56, under the lip 62. Rotation of the knurled surface 65 of the bushing then causes the foot 60 to move between its locked and unlocked positions, as indicated by the arrows in FIG. 3.

Figure 4B:
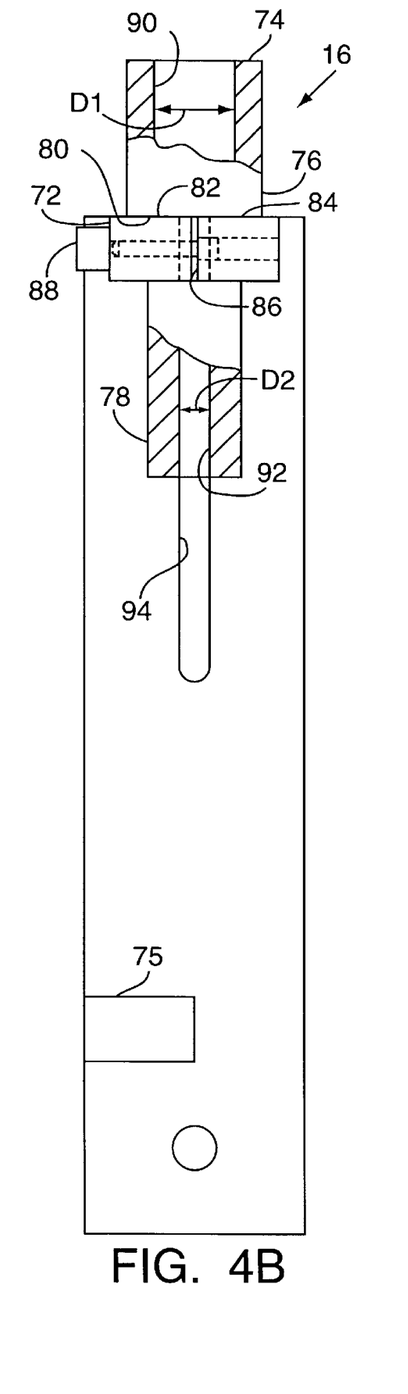
FIG. 4B is a partly in section front elevational view of the mounting arm of the apparatus of FIG. 2.
Figure 4C:
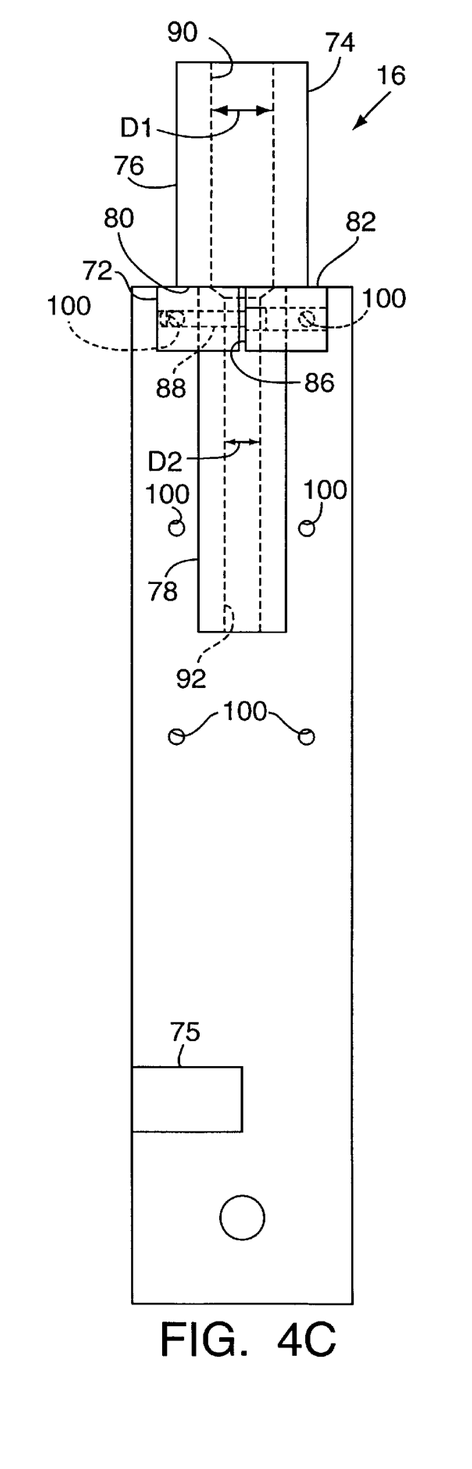
FIG. 4C is a front elevational view of an alternate embodiment of the mounting arm of the apparatus of FIG. 2.

Referring to FIGS. 4B and 4C, the mounting arm 16 of the present invention includes a first support bracket 72 mounted on the upper end of the arm, and one of a plurality of different endoscope holders 74 slidably received and retained within the first support bracket. The endoscope holder 74 defines a first cylindrical body section 76, a second cylindrical body section 78 having a reduced outer diameter in comparison to the first body section, and a lip 80 between the two sections. The lip 80 functions as a stop, and is seated against the upper surface 82 of the first support bracket 72 when the endoscope holder 74 is received within the bracket. In order to retain the endoscope holder 74, the first support bracket 72 defines a split-collar construction forming an aperture 84 for receiving the second cylindrical body section 78 of the endoscope holder. A slot 86 is formed through the first support bracket 72, and a fastener 88 is threaddedly engaged with the first support bracket through the slot to move the opposing sides of the bracket toward and away from each other with rotation of the fastener, and thereby engage and release the endoscope holder mounted within the bracket. A second support bracket 75 is spaced below the first support bracket and mounted to the base of the mounting arm 16, in order to engage and support the distal end of an endoscope at a predetermined distance from each target mounted on the carrier 20.

As indicated above, in the preferred embodiment of the present invention, a plurality of endoscope holders 74 are provided, each for receiving a different size of endoscope. As best seen in FIG. 4B, the endoscope holder 74 defines a first aperture 90 extending through the first cylindrical body section 76 and having a first inner diameter D1 for receiving the eyepiece of an endoscope, and a second aperture 92 extending through the second cylindrical body section 78 and having a second inner diameter D2 for receiving the body portion of the endoscope. The first and second inner diameters, D1 and D2 respectively, vary for each of the respective endoscope holders depending on the configuration of the endoscope that the holder is designed to retain. In the preferred embodiment, the apparatus 12 is adapted to accept endoscopes having bodies defining diameters within the range of approximately 1.9 through 10.0 millimeters, lengths within the range of approximately 4 inches through 13 inches, and tip angles within the range of approximately 0 degrees through 120 degrees.

Still referring to FIG. 4B, the mounting arm 16 defines a slot 94 extending in its elongated or axial direction. As is best seen in FIG. 4A, the first support bracket 72 includes a boss 96 extending therefrom and having a shape that is complimentary to the slot 94. The boss 96 is slidably received within the slot 94 for selectively positioning the first support bracket along the slot to accommodate endoscopes of differing lengths. The first support bracket 72 is locked into position along the slot by a fastener 98. Alternatively, and as shown in FIG. 4C, the mounting arm 16 may define a plurality of aperture pairs 100 spaced relative to each other at predetermined intervals for attaching the first support bracket to the mounting arm, and to thereby accommodate endoscopes of different lengths.

Figure 5A:
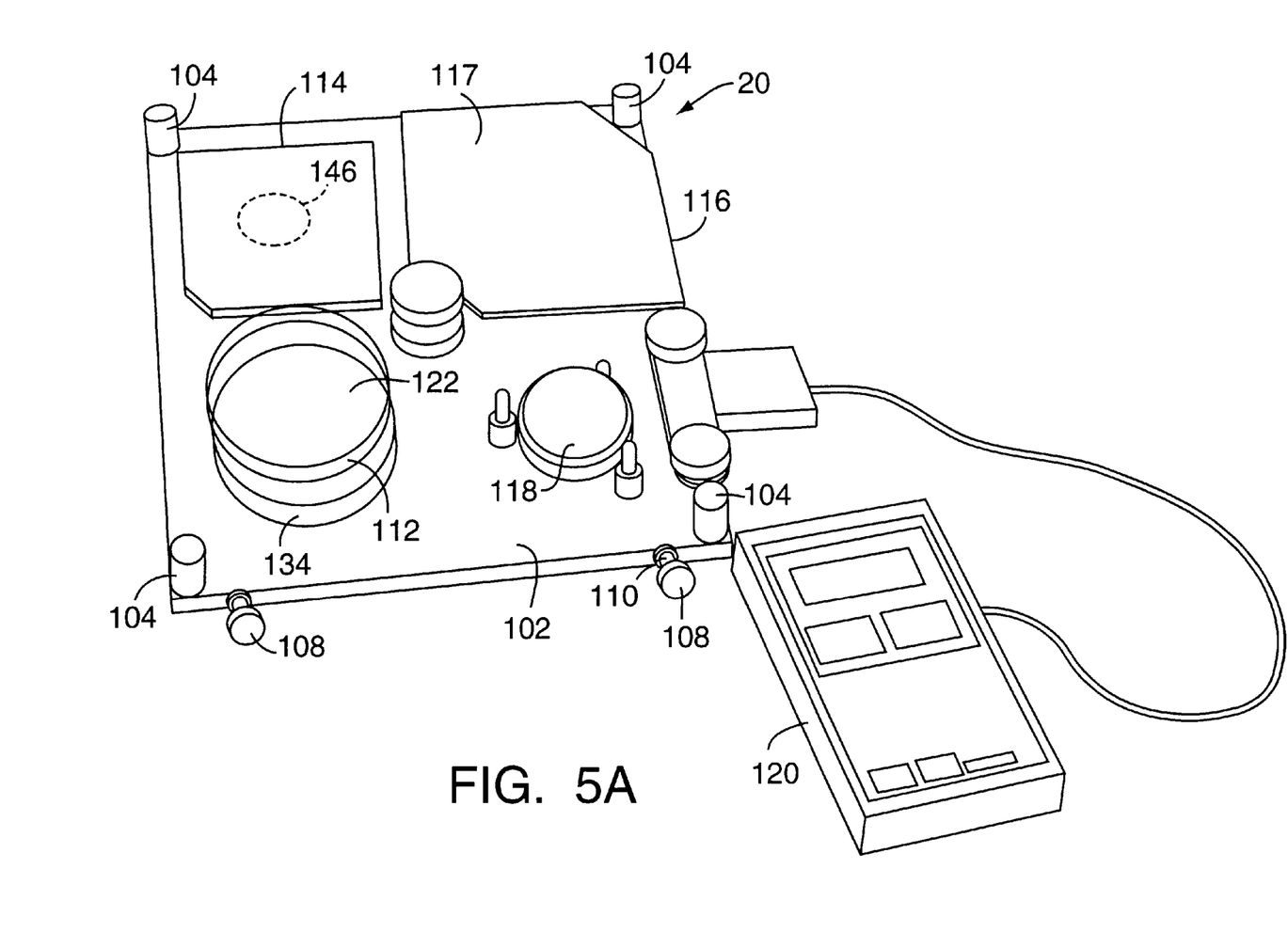
FIG. 5A is a perspective view of the carrier and associated targets of the apparatus of FIG. 2.

Turning to FIG. 5A, the carrier 20 includes a mounting surface 102 for supporting a plurality of different targets, and four legs 104 for supporting the carrier on the carrier support 40. The carrier 20 also includes two pairs of adjustable abutment members 106 (only one pair shown in FIG. 5A) mounted on opposite sides of the carrier relative to each other, with each pair spaced apart from each other on the respective carrier side. Each abutment member 106 includes a head 108 and a threaded shaft 110 connected at one end to the head and threaddedly engaged at the other end with the respective side of the carrier. With the carrier 20 mounted on the carrier support 40, as shown in FIG. 2, the respective pairs of abutment members 106 are rotated into contact with the front face of the arm support 42 to thereby maintain the carrier in an aligned configuration relative to the mounting arm 16.

As further shown in FIG. 5A, the plurality of targets located on the carrier's mounting surface 102 preferably include a reflector 112, a semi-transparent medium 114, a reflectance card 116, and a photometer 118. A light meter 120 is also connectable to the carrier 20 for use in tests involving the photometer 118. Each of the targets 112, 114, 116, and 118 are used in the performance of a different test for evaluating the performance characteristics of an endoscope as hereinafter described.

Referring to FIG. 2, the targets of FIG. 5A are each selectively aligned with the distal end of an endoscope supported on the mounting arm 16 in order to perform the respective test by sliding the carrier 20 along the groove 58 and in turn moving the foot 60 into its locked position to fix the carrier in place. Because the illustrated carrier 20 is rectangular, a single set-up allows for tests to be conducted using only two of the targets, such as the reflector 112 and photometer 118, and then the carrier must be removed, rotated 180° and repositioned in the groove 58 so that the remaining two targets, the semi-transparent medium 114 and the reflectance card 116, can be aligned with the endoscope. While a rectangular carrier has been shown and described, the present invention is not limited in this regard, and other carrier configurations can be substituted without departing from the broader aspects of the present invention. For example, the carrier 20 could be configured as a turntable mounted to the carrier support and rotatable relative to the mounting arm 16 in order to move the targets into and out of alignment with the endoscope being tested.

Figure 6:
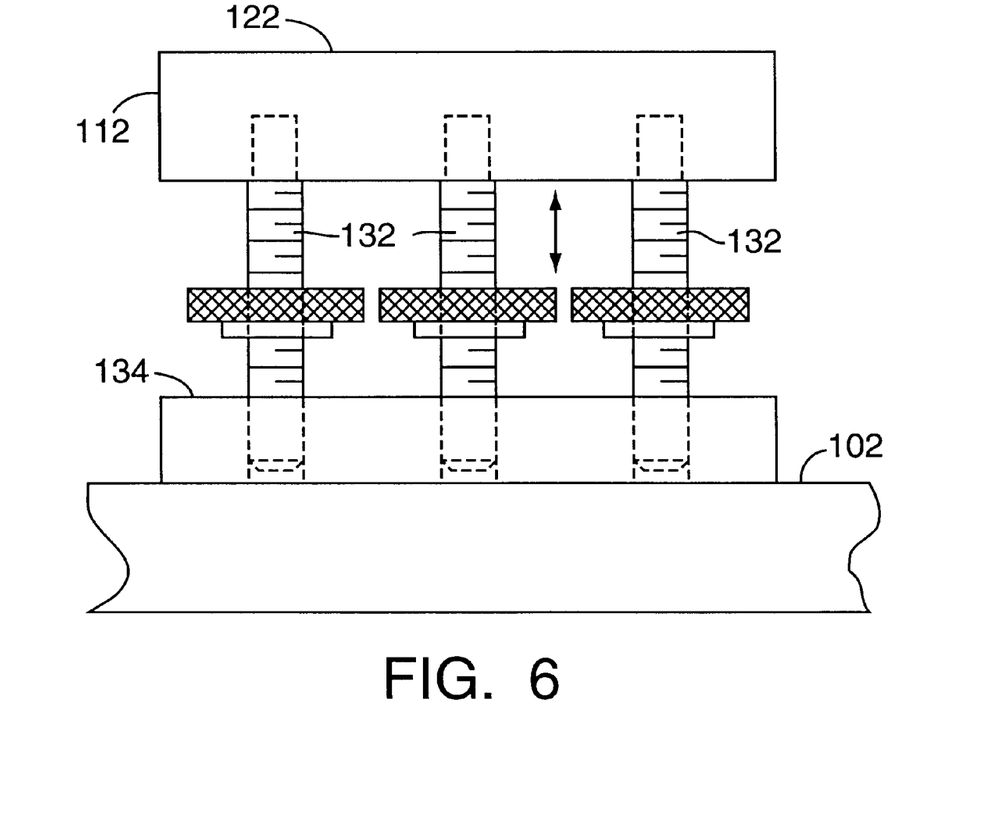
FIG. 6 is a side elevational view of the reflector of the carrier of FIG. 5A, taken from the right side.

As shown in FIGS. 5A and 6, the reflector 112 includes a mirror-like surface 122 for reflecting light back into an endoscope's distal end. Preferably, the reflector 112 is formed from a circular reflector plate formed of a low-reflectance material, such as Lucite™, which is laid over a black background to provide the mirror-like quality. The surface 122 thus creates a specular (mirror-like) reflection. When the reflector is aligned with the endoscope, the mirror-like surface 122, and the distal end of the endoscope define a predetermined distance therebetween. As shown in FIG. 6, the reflector 112 is mounted on the ends of three adjustable legs 132 which are each threadedly engaged on the other end with a mounting plate 134 seated on the carrier 20. The distance between the distal end 21 of the endoscope 18 and the mirror-like surface 122 of the reflector can be increased or decreased by rotating each of the adjustable legs, as indicated by the arrows in FIG. 6.

Figure 7:
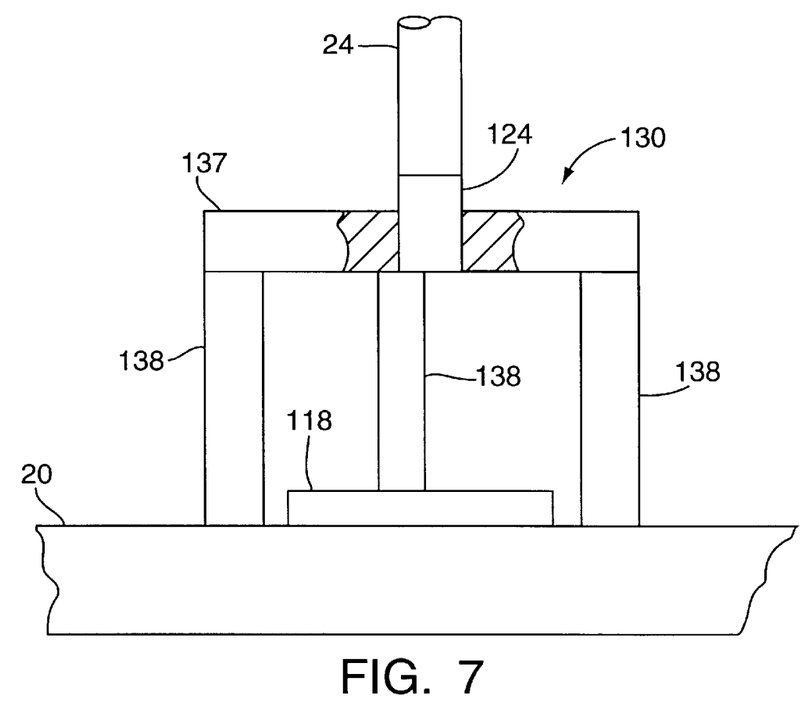
FIG. 7 is a side elevational view of the fixture for supporting an end of a fiber optic cable mounted to the carrier of FIG. 5A, taken from the left side.

As shown in FIG. 7, a relative light loss fixture 130 is seated on the carrier 20 over the photometer 118, and includes a mounting plate 137 adapted to receive end 124 of the fiber optic cable 24. The mounting plate 137 is supported on three legs 138, thereby allowing the end 124 of the fiber optic cable to be located at a predetermined distance from the photometer 118 as defined by the length of the three legs.

Figure 8:
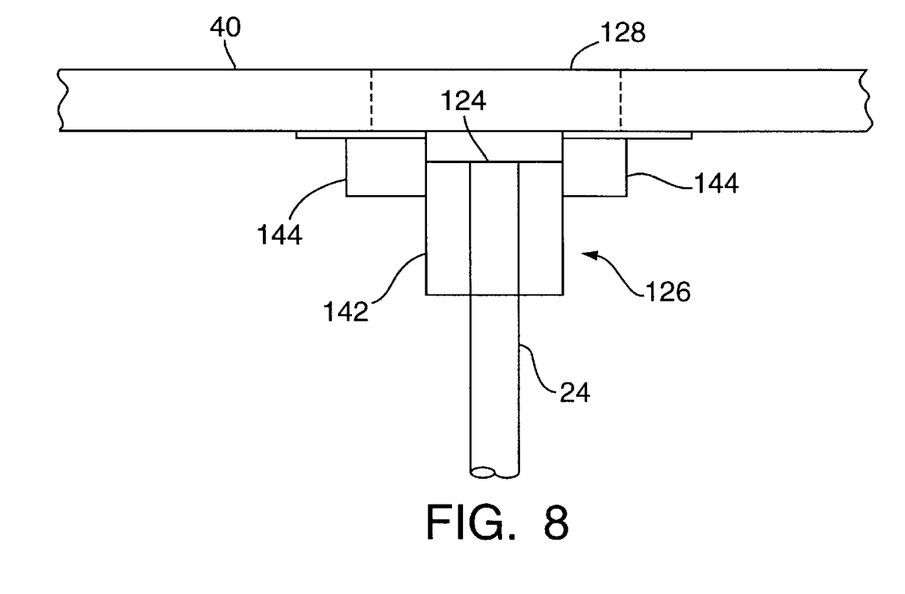
FIG. 8 is a front elevational view of the cable holder mounted to the apparatus of FIG. 2.

Turning to FIG. 8, a cable holder 126 for holding the end 124 of the fiber optic cable 24 (FIG. 1), is fixedly secured to the underside of the carrier support 40. The cable holder 126 includes a clamp 142 for receiving and retaining the end 124 of the fiber optic cable 24, and a mounting bracket 144 connected between the clamp 142 and the underside of the carrier support 40 for supporting the end of the cable below an aperture 128 defined by the carrier support 40. The cable holder 126 is secured by the mounting bracket 144 such that the end of the fiber optic cable 124 is approximately coaxial with the aperture 128. A collimating lens 145 is fixed to the underside of the carrier support 40 and covers the aperture 128 in order to collimate a light beam projected through the aperture. As shown in phantom in FIG. 5A, the carrier 20 defines an aperture 146, and the semi-transparent medium 114 is mounted over the aperture. The semi-transparent medium 114 has a transmittance which varies periodically along a predetermined direction within the medium. A beam of light which is filtered through the semi-transparent medium 114 will therefore have an intensity which varies periodically along the predetermined. In the preferred embodiment, the semi-transparent medium 114 has a transmittance which varies sinusoidally along the medium in a first direction, and is approximately constant along a second direction transverse to the first direction.

Figure 5B:
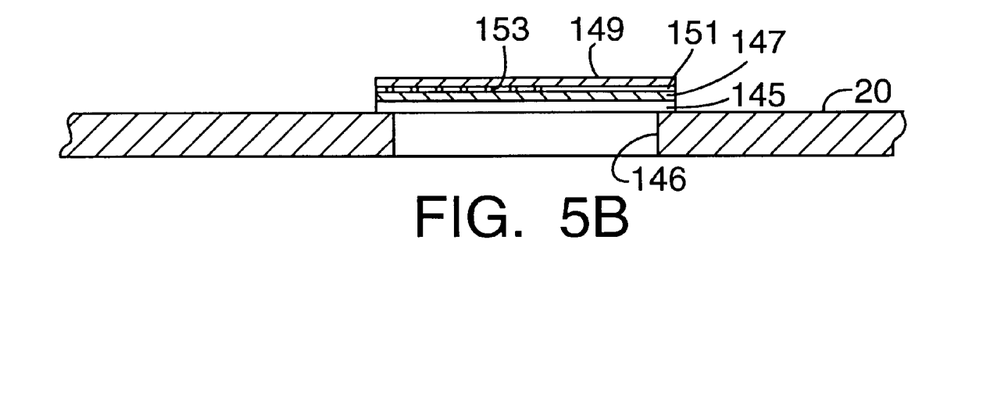
FIG. 5B is a partly in section side elevational view of the semi-transparent medium mounted on the carrier of FIG. 5B, taken from the right side.

As shown in FIG. 5B, a diffusing opal glass plate 145 is superimposed over the aperture 146, a white plastic translucent sheet 147 is superimposed over the glass plate, and the semi-transparent medium 114 is seated over the plastic sheet. A black paper mask 151 defining a plurality of apertures 153 is preferably inserted between the semi-transparent medium 149 and the white plastic layer 147 in order to block light transmission through portions of the medium, and thereby enhance points in an image corresponding to the non-masked (illuminated) portions of the medium.

The reflector 112 of FIG. 5A is used in conducting a lighted fibers test which is directed to measuring the ability of the endoscope fiber optic wires to transmit low-intensity light. In this test the light source 22 (FIG. 1) is activated and set for approximately 5% of maximum intensity. The fiber optic cable 24 is attached to the endoscope supported on the mounting arm 16, and the carrier 20 is positioned on the carrier support 40 so that the mirror-like surface 122 (FIGS. 5 and 6) is aligned with the tip 21 of the endoscope being tested, and spaced apart from the endoscope at a distance which produces a focused reflection of the lighted optical fibers at the endoscope eyepiece. The computer 36 stores the transmitted image and generates digital signals indicative of the image for evaluation.

The semi-transparent medium of FIG. 5A is used in performing the Modulation Transfer Function (MTF) Test. The (MTF) of an endoscope at a predetermined spatial frequency is equivalent to measuring the modulation transfer ratio (MTR) of the endoscope while it transmits an image having an intensity which varies along a predetermined direction at the predetermined spatial frequency. The MTR is a measure of the change in an image's modulation after transmission through the endoscope. The image modulation is roughly correlated with the contrast (sharpness) of the image. The endoscope generally reduces the modulation of a transmitted image, so that the transmitted image is not as sharp as the image received at the endoscope tip. The modulation at a location in an image is defined by the maximum intensity and the minimum intensity at that location as follows:

modulation=(maximum intensity−minimum intensity)÷(maximum intensity+minimum intensity)

The MTR is defined as

MTR=modulation of image after transmission÷modulation of image before transmission The intensity variation in the image after transmission is generally less than the intensity variation in the image before transmission. In other words, transmission through the endoscope reduces the sharpness of the image. The MTF test is directed to measuring this reduction in sharpness.

In conducting the MTF test, the light source 22 (FIG. 1) is activated and set for approximately 50% of maximum intensity. The end 124 of the fiber optic cable 24 (FIG. 1) is attached to the cable holder 126 under the aperture 128 (FIG. 8) to thereby project light through the aperture. The carrier 20 is positioned so that the semi-transparent medium 114 is aligned with the tip of the endoscope being tested. The beam transmitted from the end of the fiber optic cable 24 is transmitted through apertures 128 and 146, the glass plate 145, the plastic sheet 147, and the semi-transparent medium 114. The glass plate 145 and plastic sheet 147 together diffuse the beam from the fiber optic cable, creating a beam of substantially uniform intensity, and the semi-transparent medium 114 in turn filters the substantially uniform intensity beam to generate a beam which varies sinusoidally along a predetermined direction. The computer 36 stores the data corresponding to the transmitted beam and generates digital signals indicative of that data for evaluation.

The reflectance card 116, of FIG. 5A, defines a non-specular reflective surface 117 which, instead of forming a mirror-like reflected image, diffuses reflected light. The reflectance card is used in conducting the reflective symmetry test which is directed to measuring the reflective symmetry of light exiting the eyepiece of an endoscope. An ideal endoscope transmits a beam having an intensity which is circularly symmetrical about the center of the light. Thus, when the ideal endoscope transmits an image of uniform intensity from its tip end to its proximal end, the intensity in the center of the transmitted image is greatest, and the intensity decreases at locations in the transmitted image spaced radially from the center. All points which are equally distant from the center of the transmitted image have equal intensities, and the intensity at the periphery of the transmitted image is lowest. In actual (non-ideal) endoscopes, distortion in the circular symmetry of the transmitted image indicates damaged optical fibers.

In performing the reflective symmetry test, the light source 22 (FIG. 1) is activated and set for approximately 25% of its maximum intensity. The fiber optic cable 24 is attached to the endoscope supported on the mounting arm 16, and the carrier 20 is positioned so that the reflectance card 116 is aligned with the endoscope tip. The video system 28 (FIG. 1) records the image transmitted by the endoscope. The transmitted image is received by the computer 36 and the computer in turn generates digital signals indicative of the transmitted image. The distortion in the reflected image is then evaluated to ascertain the existence of any damaged fibers in the endoscope being tested.

The photometer 118 of FIG. 5A is used in the performance of a light loss test which is directed to measuring the reduction in the intensity of light after transmission through the endoscope. In general, the test comprises measuring two quantities: the intensity of light which exits the fiber optic cable ("light-in") and the intensity of light transmitted through the endoscope ("light-out").

In performing the light loss test, the light source 22 (FIG. 1) is activated and set for approximately 25% of maximum intensity and preferably left on for at least 10 minutes to allow the light source to reach the intensity for which it is set. Referring to FIG. 7, the end 124 of the fiber optic cable 24 (FIG. 1) is coupled to the fixture 130, such that the end of the fiber optic cable is supported at a predetermined distance relative to the photometer 118 as defined by the legs 138. The photometer intensity reading is then recorded by the light meter 120, and this intensity reading is designated the "light-in".

After the light-in intensity is recorded, the fiber optic cable is removed from the fixture 130 and attached to an endoscope 26 supported on the mounting arm 16 (FIG. 1). The angular position of the mounting arm 16 is adjusted to correspond to the angular position of the tip angle of the endoscope being tested, and the position of the carrier 20 is adjusted so that the photometer 118 is aligned with the endoscope tip. The photometer intensity reading is then recorded by the light meter 120, and this intensity reading is designated the "light-out". The light-in and light-out readings can then be compared in order to evaluate the condition of the fiber optic wires in the endoscope.

While preferred embodiments have been shown and described, various modifications and substitutions may be made without departing from the spirit and scope of the invention. Accordingly, it is to be understood that the present invention has been described by way of example, and not by limitation.

What is claimed is:

1. An apparatus for evaluating the performance characteristics of endoscopes, comprising:
    a frame including a carrier support;
    a mounting arm coupled to the frame and movable relative to the carrier support for supporting an endoscope and adjusting the position of the endoscope relative to the carrier support;
    a carrier mounted on the carrier support adjacent to the mounting arm and movable relative to the mounting arm for adjusting the position of the carrier relative to an endoscope on the arm; and
    at least one target mounted on the carrier for evaluating the performance characteristics of an endoscope supported on the arm.

2. An apparatus for evaluating the performance characteristics of endoscopes as defined by claim 1, further comprising:
    a plurality of endoscope holders, each defining an aperture for receiving and retaining a different size endoscope; and wherein
    the mounting arm includes a first support bracket defining an aperture for receiving each of the plurality of endoscope holders.

3. An apparatus for evaluating the performance characteristics of an endoscope as defined by claim 2, wherein the mounting arm defines an elongated slot, and the first support bracket is slidably received within the slot for selectively positioning the first support bracket along the slot to accommodate endoscopes of different lengths.

4. An apparatus for evaluating the performance characteristics of endoscopes as defined by claim 2, wherein:
    the mounting arm defines a plurality of apertures spaced relative to each other for attaching the first support bracket to the mounting arm; and wherein
    the apertures are positioned at predetermined locations along the mounting arm for adjusting the position of the first support bracket to accommodate endoscopes of different lengths.

5. An apparatus for evaluating the performance characteristics of endoscopes as defined by claim 2, wherein the mounting arm further includes a second support bracket spaced apart from the first support bracket for supporting a distal end of an endoscope.

6. An apparatus for evaluating the performance characteristics of endoscopes as defined by claim 1, wherein:
    the frame includes a plurality of angular indicia incrementally spaced relative to each other for adjusting the angular position of the mounting arm relative to the at least one target to correspond to the each of a plurality of different endoscope tip angles.

7. An apparatus for evaluating the performance characteristics of endoscopes as defined by claim 1, wherein:
    the frame further includes an arm support mounted rearwardly of and adjacent to the carrier support; and wherein
    the mounting arm is coupled to the arm support and movable relative to the carrier support for adjusting the angular position of an endoscope mounted on the arm relative to the at least one target.

8. An apparatus for evaluating the performance characteristics of endoscopes as defined by claim 1, wherein the frame includes means for guiding the carrier along the carrier support for adjusting the position of the at least one target relative to an endoscope on the mounting arm.

9. An apparatus for evaluating the performance characteristics of endoscopes as defined by claim 8, wherein the means for guiding includes a groove defined by at least one of the carrier and the carrier support, and the other defines a guide received within the groove.

10. An apparatus for evaluating the performance characteristics of endoscopes as defined by claim 9, wherein the guide includes means for releasably securing the carrier in a selected position.

11. An apparatus for evaluating the performance characteristics of endoscopes as defined by claim 1, wherein the at least one target mounted on the carrier is a reflector defining a substantially mirror-like surface for reflecting light back onto an endoscope supported on the mounting arm.

12. An apparatus for evaluating the performance characteristics of endoscopes as defined by claim 11, wherein:

the reflector includes means for adjusting the space between the distal end and the mirror-like surface.

13. An apparatus for evaluating the performance characteristics of endoscopes as defined by claim 1, wherein the at least one target is a photometer for measuring light input to an endoscope, and light output from an endoscope.

14. An apparatus for evaluating the performance characteristics of endoscopes as defined by claim 13, further comprising:

a fixture mounted to the carrier adjacent to the photometer for receiving an end of a fiber optic cable and for spacing the end of the cable at a predetermined distance from the photometer.

15. An apparatus for evaluating the performance characteristics of endoscopes as defined by claim 1, wherein:

the carrier support defines a first aperture formed therethrough adjacent to one end of the mounting arm; and the carrier defines a second aperture alignable with the first aperture; and further comprising a fiber optic cable supportable on the opposite side of the first aperture relative to the mounting arm for transmitting a beam through the first and second apertures; and a semi-transparent medium mounted over the second aperture for performing a modulation transfer function test on an endoscope.

16. An apparatus for evaluating the performance characteristics of endoscopes as defined by claim 1, wherein one of the plurality of targets is a reflectance card defining a non-specular reflective surface for performing a reflective symmetry test on an endoscope.

* * * * *